United States Patent [19]

Namkung et al.

[11] Patent Number: 5,164,669

[45] Date of Patent: Nov. 17, 1992

[54] METHOD OF CHARACTERIZING RESIDUAL STRESS IN FERROMAGNETIC MATERIALS USING A PULSE HISTOGRAM OF ACOUSTIC EMISSION SIGNALS

[75] Inventors: Min Namkung, Tabb; Peter W. Kushnick, Williamsburg; William T. Yost; John L. Grainger, both of Newport News, all of Va.

[73] Assignee: The United States of America as represented by the Administrator of the National Aeronautics and Space Administration, Washington, D.C.

[21] Appl. No.: 555,864

[22] Filed: Jul. 23, 1990

[51] Int. Cl.[5] .................... G01B 33/12; G01B 7/24; G01B 17/04; G01N 29/18
[52] U.S. Cl. .................... 324/209; 73/598; 73/801; 324/227; 324/232
[58] Field of Search ............... 324/209, 227, 232, 235; 73/587, 597, 598, 601, 760, 779, 801

[56] References Cited

U.S. PATENT DOCUMENTS

| | | |
|---|---|---|
| 4,319,189 | 3/1982 | Cullum, Jr. et al. |
| 4,408,160 | 10/1983 | King et al. .......................... 324/209 |
| 4,497,209 | 2/1985 | Kwun et al. .......................... 73/601 |
| 4,599,563 | 7/1986 | Tiito et al. ...................... 324/209 X |
| 4,689,558 | 8/1987 | Ruuskanen et al. ................. 324/209 |
| 4,709,210 | 11/1987 | Pond . |
| 4,912,411 | 3/1990 | Allison et al. .................. 324/209 X |

FOREIGN PATENT DOCUMENTS

| | | |
|---|---|---|
| 0111442 | 7/1982 | Japan ................................... 324/209 |
| 0112257 | 6/1984 | Japan ................................... 324/209 |

OTHER PUBLICATIONS

Low-Field Magnetoacoustic Residual Stress Measurement In Steel, dated Sep. 18-20, 1985—M. Namkung et al.

*Primary Examiner*—Gerard R. Strecker
*Attorney, Agent, or Firm*—Kevin B. Osborne

[57] ABSTRACT

The invention is a method and apparatus for characterizing residual uniaxial stress in a ferromagnetic test member by distinguishing between residual stresses resulting from positive (tension) forces and negative (compression) forces by using the distinct and known magnetoacoustic (MAC) and a novel magnetoacoustic emission (MAE) measurement circuit means. A switch permits the selective operation of the respective circuit means.

11 Claims, 6 Drawing Sheets

METHOD OF CHARACTERIZING RESIDUAL STRESS IN FERROMAGNETIC MATERIALS USING A PULSE HISTOGRAM OF ACOUSTIC EMISSION SIGNALS

ORIGIN OF THE INVENTION

The invention described herein was made jointly in the performance of work under NASA contracts NAS1-18000 and NAS1-18599 and employees of the U.S. Government and is subject to the provisions of Section 305 of the National Aeronautics and Space Act of 1958, as amended, Public Law 85-568 (72 Stat. 435;42 USC 2457) and 35 USC 202(8). In accordance with 35 USC 202, the contractor elected not to retain title.

BACKGROUND OF THE INVENTION

1. Field of the Invention

The invention relates to method and apparatus for characterizing residual stress in ferromagnetic members and more particularly to such method and apparatus for distinguishing between residual stresses resulting from compression and tension forces in ferromagnetic test members.

2. Description of the Prior Art

Residual stress characterization in ferromagnetic members such as steel load bearing structural beams and girders, wheels, gears and the like is a difficult and critical challenge. While a magnetoacoustic (MAC) method for detecting the presence of residual compression without requiring calibration standards is known, this technique is not capable of detecting the presence of residual tension in a ferromagnetic member and thus characterizing or distinguishing between the two distinct forms of residual stress.

Another technique generally known as magnetoacoustic emission (MAE) (as shown in U.S. Pat. No. 4,408,160) is capable of detecting the presence of residual stress in ferromagnetic materials resulting from both compression and tension forces without the capability of distinguishing between the two.

Numerous other techniques for sensing residual stress in ferromagnetic members are also generally known. For instance, x-ray diffraction is a method capable of quantitatively characterizing the surface residual stress state in metallic objects while the ultrasonic birefringence technique, in principle, is capable of measuring bulk residual stress in solid materials.

However, while x-ray diffraction is the only quantitative method known to the inventors that senses the amplitude of residual stress, a major disadvantage of this technique is that its use is limited to a shallow surface region of metallic objects and the surface preparation necessary to obtain reliable data.

The ultrasonic birefringence technique is in general extremely sensitive to the intrinsic structural properties of members examined, i.e., textures in polycrystals. The effect of texture on the observed birefringence is comparable or even larger than that due to residual stress. Thus this technique requires the use of ultrasonic shear waves with their polarization perpendicular to each other. In practical application it is impossible to maintain the constant mechanical coupling between the ultrasonic transducer and the test object for the two angular positions of the transducer.

The Barkhausen technique as described in the aforementioned U.S. Pat. No. 4,408,160 measures discontinuity in magnetization as a form of a magnetic acoustical noise signal using a pickup coil as a sensor. A disadvantage of this method is that when it is necessary to use an external magnetic core to induce a strong magnetic flux density in a test object, the magnetic noise signal from the core interferes with the acoustical emission signals produced in the test objects. Further there is no way to distinguish or characterize the residual stress as to its cause—forces in compression or tension on the test object.

SUMMARY OF THE INVENTION

An object of the invention is to overcome the disadvantages of the prior art by providing method and apparatus for characterizing residual stress in ferromagnetic members resulting from the forces of compression and tension.

Yet another object of the invention is to provide method and apparatus for distinguishing between compression and tension forces producing residual stress in ferromagnetic members.

Still another object of the invention is to provide method and apparatus using both magneatoacoustic circuit means for sensing any residual compression stress in a ferromagnetic member and magnetoacoustic emission circuit means for sensing an undesirable level of residual tension stress in the same ferromagnetic member and comparison circuit means for characterizing the sensed residual stress as resulting from either compression or tension forces and the uniaxial stress axis in said ferromagnetic member on which applied.

BRIEF DESCRIPTION OF THE DRAWINGS

The above and numerous other objects that may be achieved by the method and a preferred apparatus of the invention will become apparent from the following Detailed Description when read in view of the appended drawings wherein.

BRIEF DESCRIPTION OF THE INVENTION

Several unique phenomena have been observed during the irreversible domain wall motion in a ferromagnet. As a result the Barkhausen and ΔE-type effects have been extensively studied due to their sensitivity to the material properties and residual stress states. Between these two effects, the former is based on the abrupt motion of domain wall over pinning sites and the latter is based on the progressive rearrangement of domain structure following the magnetization process. The ΔE type effect is the change in material stiffness, or more precisely in the elastic modulus, of a material due to application of a magnetic field and is usually defined as $(E_S - E_O)/E_O$, wherein $E_S$ and $E_O$ are the elastic moduli of a particular material at the magnetically saturated and demagnetized states, respectively.

A series of acoustic noise events, which occurs almost simultaneously with the known and so called magnetic Barkhausen noise, provides a separate methodology with unique capabilities and is the base of the magnetoacoustic emission (MAE) technique. The practical application of the ΔE-type effect to NDE residual stress measurement involves measuring ΔF (B)/F, that is fractional changes in frequency of phase-locked acoustic waves as a function of net magnetic induction. This method is known as the low-field magnetoacoustic (MAC) technique.

It has been discovered that a unique feature of the MAC technique is the presence of a negative initial slope of ΔF(B)/F curves when net magnetization is induced parallel to the uniaxial compressive stress axis. The detection of uniaxial compressive residual stress is, therefore, possible without requiring a calibration standard.

Heretobefore, the detection of uniaxial tensile residual stress, however, has not been possible due to the fact that ΔF(B)/F curves obtained under tension lie under that of the unstressed state except for certain types of steel.

By comparing the uniaxial stress dependence of MAE measurements with MAC measurements performed with the same test member (TM) in accordance with this invention, it is possible to detect the presence of uniaxial residual tensile stress provided there is a sufficient magnetic field intensity and, at the same time, there is an absence of compressive uniaxial residual stress in the object. Thus the combination of the MAE and MAC techniques as described hereinafter permits the reliable characterization of the residual stress state in a ferromagnetic test member (TM), the two techniques complementing each other.

Maximum Stress Effects on MAE Responses

The lattice and ferromagnetic systems interact with each other through the magnetoelastic interaction. The minimization of this interaction energy causes an anisotropic deformation of lattice unit cells, called spontaneous magnetostriction. An application of uniaxial stress adds an angular dependence, which involves the angle between the uniaxial stress axis and the magnetization vector of each domain, to the interaction.

As a result, the ferromagnetic state readjusts first by moving the domain walls. The rotation of domain magnetization due to uniaxial stress is possible but is negligible in iron and most of iron base alloys. For ferromagnets with positive spontaneous magnetostriction coefficients, the domains align parallel to the tensile stress axis, and they align perpendicular to the compressive stress axis.

Two types of domain walls exist in these ferromagnets: 90° and 180° walls. Under uniaxial tension, the area of 90° domain walls gradually decrease upon the increase in stress amplitude and the domain structure becomes uniaxial. Under uniaxial compression, however, the domain structure is multi-axial and the area of 90° domain walls directly affected by the magnetic field applied parallel the stress axis, begins to increase slightly. After reaching its maximum, the area of these 90° domain walls begins to decrease as the magnitude of compressive stress increases.

The main factors that determine the spectral characteristics of MAE patterns are the area of 90° domain walls and the rate of their movements, and the state of lattice defects. Since the application of uniaxial stress affects the area of 90° domain walls, the uniaxial stress dependence of MAE generation is expected to follow that of 90° domain wall area.

The axial symmetry of domain structure about the uniaxial stress axis is preserved with an external field applied in any other direction. Previous work on the MAC measurements showed that the interpretation is possible—though more difficult for the results obtained by applying the magnetic field perpendicular to the uniaxial stress axis. This is also true for the MAE measurements.

In an experiment, a standard sample of HY-80 steel cast block which had not been subjected to any stress-relief heat treatment was originally machined into a cylindrical bar and then machined to obtain a rectangular cross-section of 16 mm × 14 mm for a gauge length of 105 mm. Uniaxial stress was applied up to ±200 MegaPascal (MPa) in intervals of 25 MPa. For the MAE measurements, 20 Hz sine wave output from the power supply/amplifier PS was used to activate a pair of electromagnets having C-shaped cores. For the MAC measurements, 5 MHz compressional waves were propagated perpendicular to the uniaxial stress axis in the pulse-echo mode. A description of these experimental procedures follows.

Figure 1:
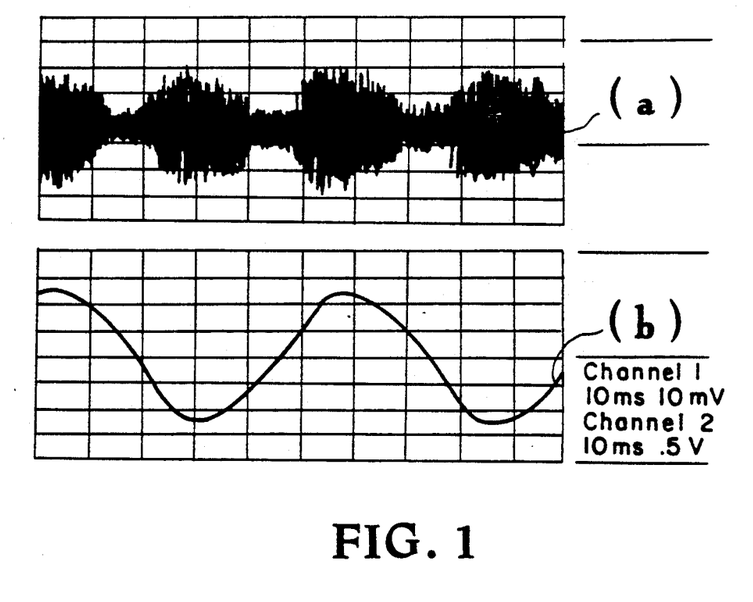
FIG. 1 illustrates the MAE spectrum, upper slope trace and corresponding pickup coil (PC) output waveform, lower slope trace obtained by applying an AC magnetic field in parallel to the cylinder axis of a standard formed of ferromagnetic material.

Referring now to the drawings, FIG. 1 shows the MAE spectrum (a) and the corresponding output (b) of a pickup coil PC of a test member TM in the unstressed state and an AC magnetic field applied parallel to the cylindrical axis. The distortion in the pickup coil PC output (b) is due to the eddy current generated by opposing magnetic flux changes in the sample. The MAE spectra activity (a) is seen to be consistent with the shape of output (b) of the pickup coil, i.e., the MAE spectra pulse amplitude (a) is generally higher where the slope of the output (b) of pickup coil PC is steeper.

Figure 2:
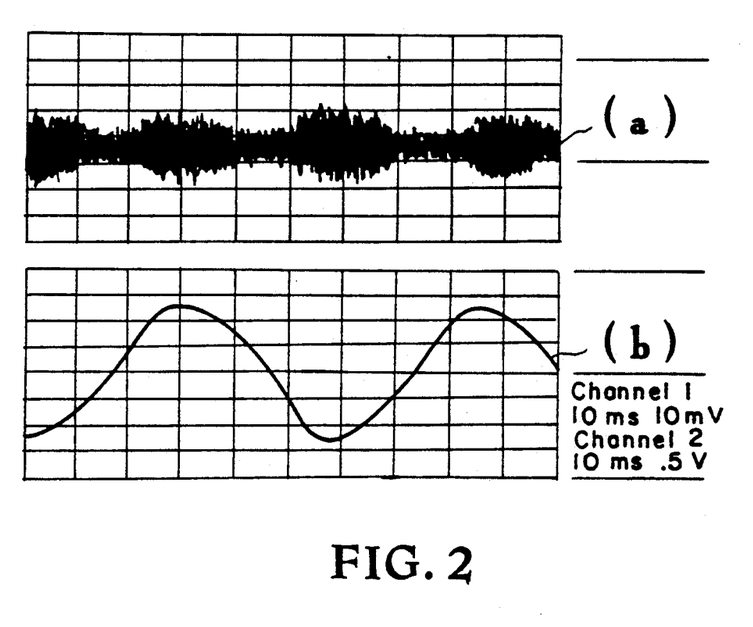
FIG. 2 illustrates the MAE spectrum and corresponding pickup coil (PC) output waveform obtained by applying an AC magnetic field parallel to the cylindrical axis of a standard sample formed of ferromagnetic material under uniaxial tensile stress.

The effect of applied tension is seen to decrease the MAE spectra amplitude. FIG. 2 shows the results obtained with 100 MPa applied parallel to the cylindrical axis of the test member TM. The output (b) of pickup coil PC is seen here to be slightly more distorted compared to that shown in FIG. 1. This is because 180° domain walls begin to dominate the domain structure under tension and the rate of the domain wall motion-induced flux change becomes higher. It has been found that the effect of small amplitude uniaxial compression increases the MAE spectrum activity (a) as shown in FIG. 2.

Figure 3:
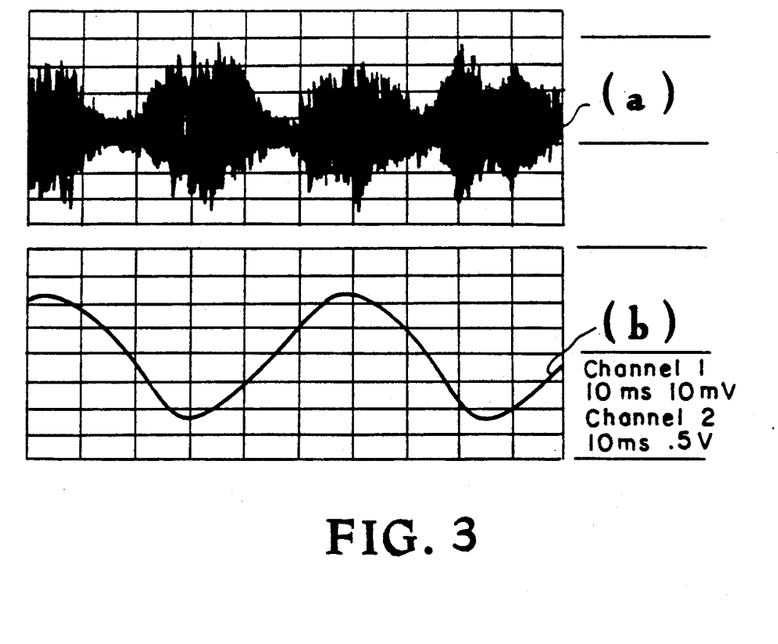
FIG. 3 illustrates the MAE spectrum and corresponding pickup coil (PC) output waveform obtained by applying an AC magnetic field parallel to the cylindrical axis of a standard formed of ferromagnetic under uniaxial compressive stress.

FIG. 3 shows the results obtained at −50 MPa where the amplitude of the MAE burst (a) is seen to be enhanced and the output (b) of pickup coil PC is less distorted compared to that shown in FIG. 1. Thus the results in FIG. 3 and indicate the enhanced activity of 90° domain walls expected by the uniaxial stress-induced domain alignment. More important, however, are the asymmetry and the appearance of a double peak structure in the MAE burst (a) of FIG. 3. These are due to the motion of 90° domain walls that is significantly slowed down.

Figure 4:
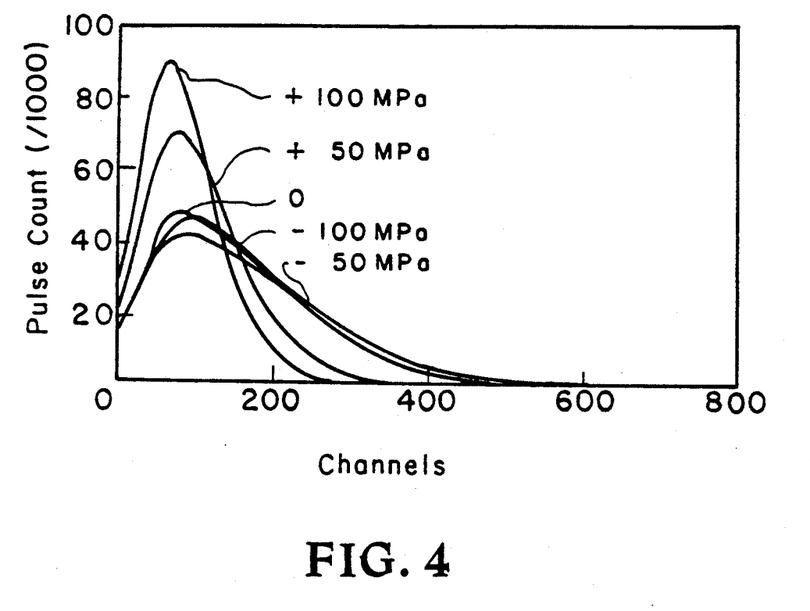
FIG. 4 illustrates histogram waveforms corresponding to the MAE spectra obtained from applying an AC magnetic field parallel to a cylindrical axis of a standard sample of ferromagnetic material through a plurality of applied uniaxial stress forces ranging from descending positive or tensile stresses through zero stress to increasing negative or compressive stresses.
Figure 9:
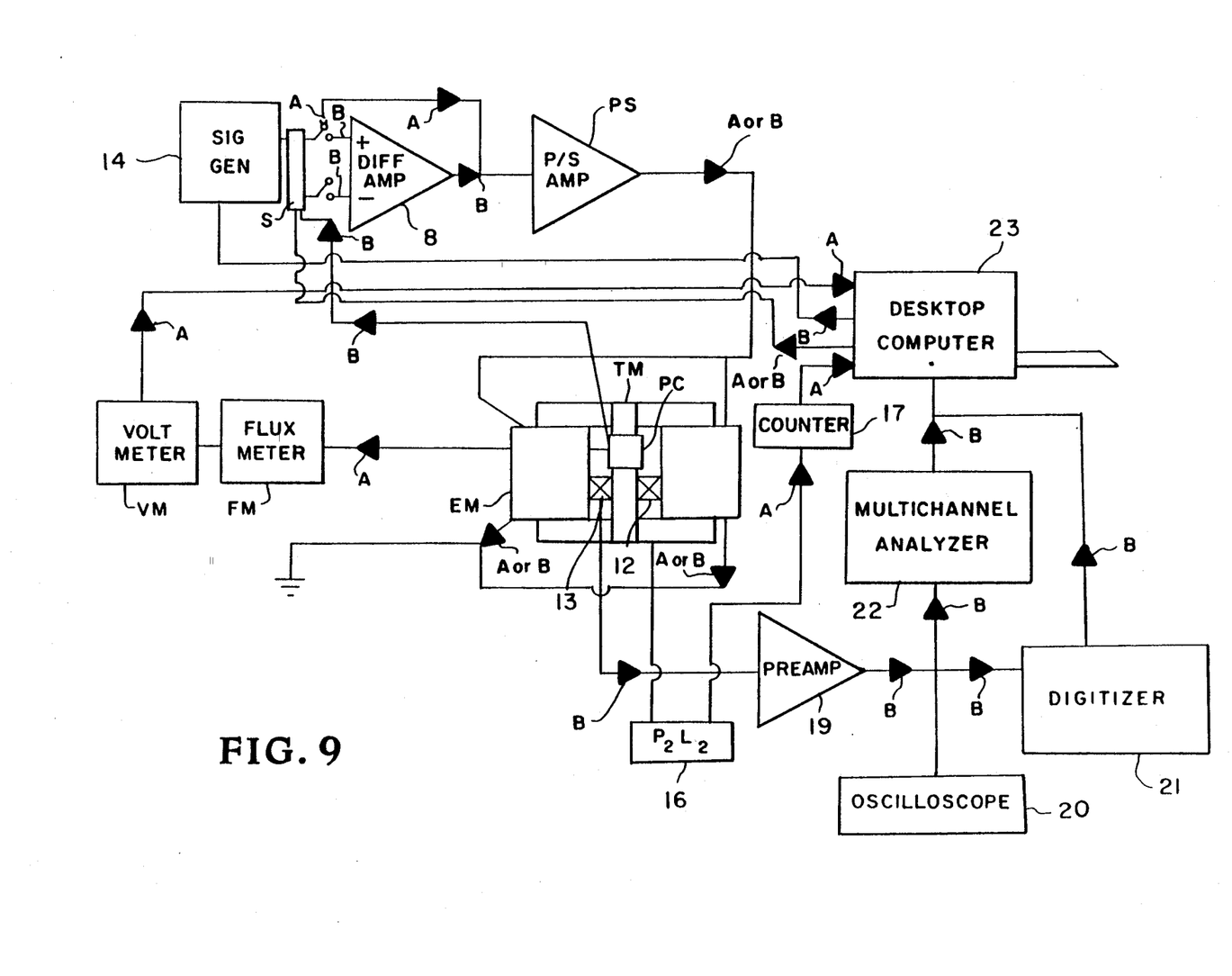
FIG. 9 is an electrical schematic of a preferred embodiment of the invention for practicing the method of the invention.

FIG. 4 shows the MAE spectra histograms generated and displayed by the circuit shown in FIG. 9. These MAE spectra histograms represent the pulse height distributions of the MAE spectra obtained at the unstressed state and at selected levels of uniaxial stress with the AC field applied parallel to the stress axis. The results clearly indicate that the effect of tension is seen to increase the width of pulse height distribution at low stress levels, and begins to decrease it as the tensile stress increases to higher undesirable values. This narrowing of the width of pulse height distribution gives rise to an initial and relatively high peak in the histogram waveform. Zero residual stress results in a wide, broad crown in the histogram waveform while increasing negative or compressive forces lower and further widen the crown in the pulse height distribution histogram waveform.

Figure 5:
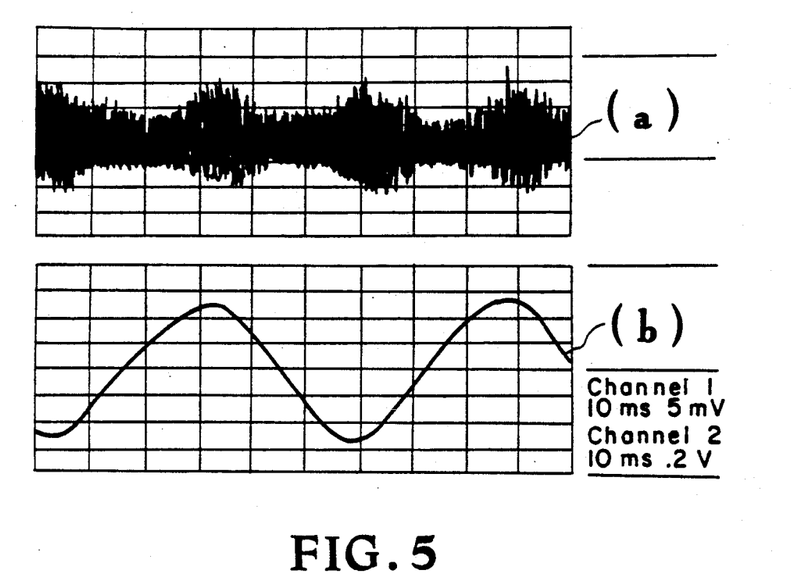
FIG. 5 illustrates the MAE spectra and corresponding pickup coil (PC) waveform results obtained by applying a uniaxial negative compressive stress to a standard sample of ferromagnetic material with an AC magnetic field applied perpendicular to the stress axis.

FIG. 5 shows the results obtained at −50 MPa by applying an AC magnetic field perpendicular to the uniaxial stress axis of the test sample. None of the results obtained with this magnetization scheme showed any particular form of MAE pattern under uniaxial stress. For a direct comparison, each pulse height distribution histogram is fitted to the Gaussian distribution, $N(x) = N_0 \exp(\sigma^2 x^2)$ by means of a computer 23 where the width of the distribution is directly influenced by the magnitude of $\sigma$. A computer 23 that may be used for processing the output of a multi-channel analyzer 22 to perform this operation is an HP9000, Series 300 computer manufactured by Hewlett-Packard Corporation of Cupertino, Calif.

Figure 6:
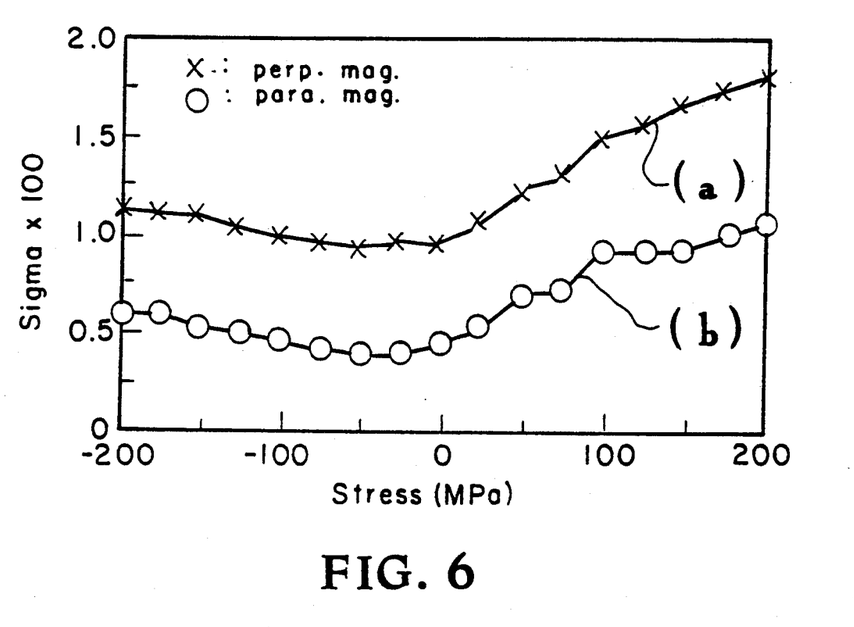
FIG. 6 illustrates waveforms resulting from a Gaussian fitting of the MAE histograms obtained at varying uniaxial stress levels for applied perpendicular and parallel AC magnetic fields respectively.

The results are summarized in FIG. 6. As seen in this figure, the trend in the uniaxial stress effects on the MAE spectral characteristics is not particularly different for two different magnetization schemes. This means that the MAE technique alone cannot distinguish between the presence of tensile residual stress and compressive residual stress.

While the extremely low level of MAE activity under relatively high tensile stress shown in FIG. 4 can indicate the presence of residual tensile stress, a sufficient AC magnetic field must exist in the test member TM and the presence of residual compressive stress excluded. A feedback circuit from pickup coil PC is provided to assure that the magnetic field in the test member TM follows the sinewave generated by a power supply.

Figure 7:
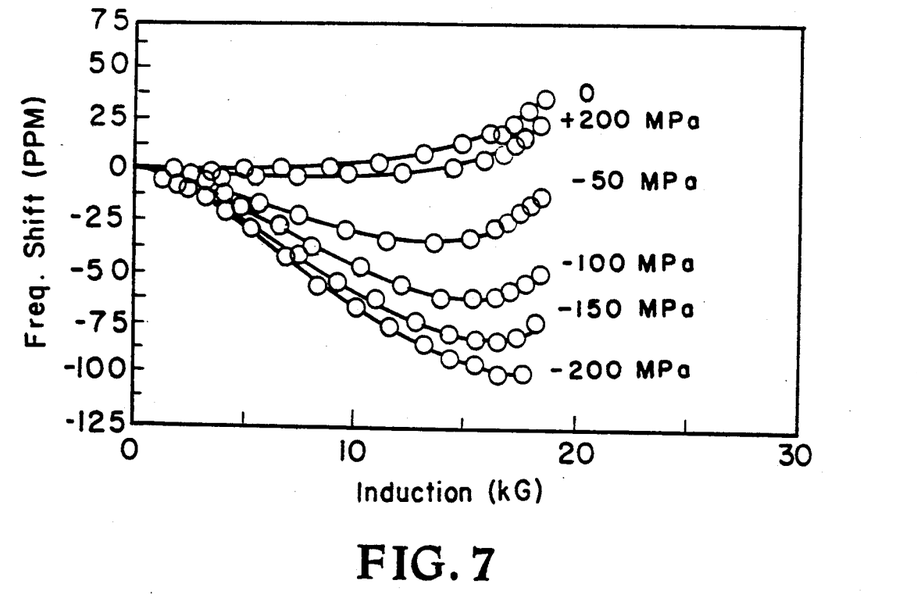
FIG. 7 illustrates the results of MAC measurements obtained from a positive tensile uniaxial stress state through a uniaxial unstressed state and an increasing range of negative compressive uniaxial stresses with an external magnetic field applied parallel to the uniaxial stress axis.
Figure 8:
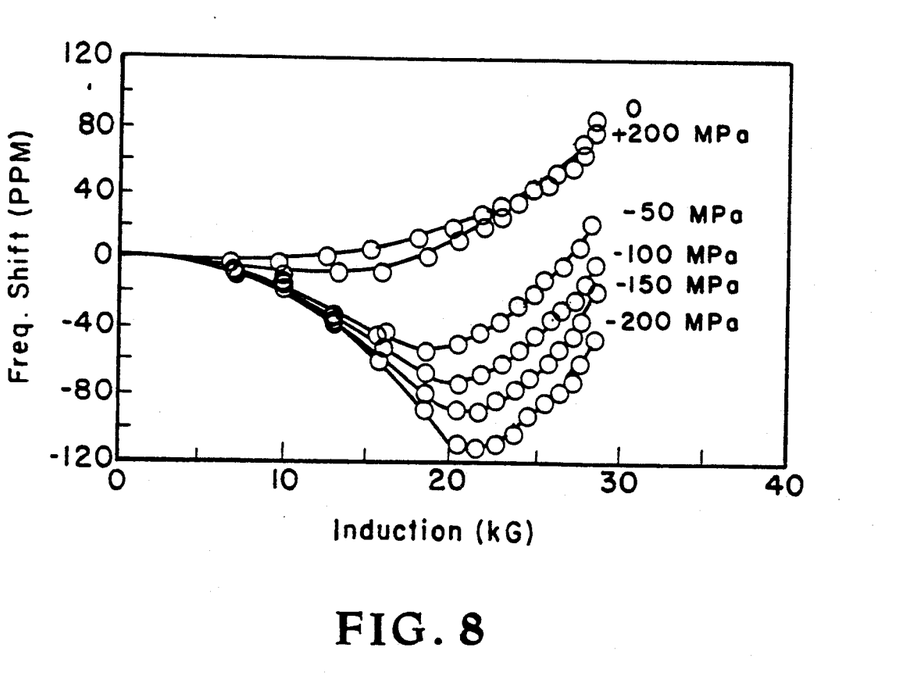
FIG. 8 illustrates the resulting waveforms as in FIG. 7 with the external magnetic field applied perpendicular to the uniaxial stress axis.

Results of MAC measurements in accordance with the invention are shown in FIGS. 7 and 8. FIG. 7 shows the results obtained by incrementally applying DC magnetic field parallel to the uniaxial stress axis. As seen there is almost no difference between the curves obtained in the unstressed state and under 200 MPa. All the other tension curves are positioned under these two curves. The curves under compression, however, show a good separation between the stress levels.

FIG. 8 shows the results obtained by applying the external field perpendicular to the uniaxial stress axis. The curves in this FIG. show similar effects of uniaxial stress to those seen in FIG. 7. While the steep negative slope under uniaxial compression shown in FIG. 8 has not been observed in other types of steel samples with such a magnetization scheme, the results in both FIGS. 7 and 8 nevertheless reaffirm that the MAC technique is capable of detecting the presence of residual compressive stress.

With the application of an AC magnetic field parallel to the stress axis, the peak amplitude of MAE burst increased under −50 MPa, as shown in FIG. 3. Similar results were obtained at −75 MPa. Beyond this, the amplitude of the MAE burst begins to decrease as the magnitude of compressive stress increases. This is consistent with the well-known uniaxial stress-induced domain alignment in this type of ferromagnet.

The double-peak pattern and asymmetry in the MAE burst appeared in the range between approximately −50 MPa and −75 MPa. As the magnitude of compressive stress increases, the asymmetry disappears but the double-peak pattern is sustained. The compressive stress dependence of these two characteristics is explained as follows.

The double-peak pattern has been recognized as a characteristic of an MAE spectrum obtained with an AC magnetic field frequency much lower than 20 Hz as used in this invention. For example, the appearance of this pattern in an MAE burst at 0.7 Hz is well known. The double peak pattern has been attributed to the slow rate of flux change that allows the 90° domain walls to spend sufficient time between two major potential barriers that these walls encounter just before and after $\pm H_C$, where $H_C$ is the coercive field. It has been discovered in accordance with this invention that if the rate of 90° domain wall movement is lowered independently, the double-peak pattern in the MAE burst appears almost regardless of the frequency of the applied AC field.

The asymmetry in the MAE burst has also been observed previously in highly embrittled, residual stress-free, HY-80 steel samples. The effect of embrittlement in this ferromagnet is to increase the height of the effective potential barriers, resisting the 90° domain wall motion, at the grain boundaries. Each 90° domain wall moves along a different path during the field-induced domain wall motion process. Some of these domain walls encounter stronger barriers and fail to execute their complete motion. The rate of 90° domain movements under this condition should be different for the motion toward the top of the barrier and that in the opposite direction. Since the MAE activity is a function of the rate of 90° domain wall movement, an asymmetry appears as the potential barriers are enhanced. If the external magnetic field-induced driving force is such that some 90° domain walls fail to complete their motion, the asymmetry in the MAE burst also appears.

Therefore, it is shown the effect of the presence of uniaxial compression is to slow down the 90° domain wall motion that is induced by an AC magnetic field applied parallel to the stress axis. This is consistent with what can be expected from the various interactions. Upon the application of uniaxial compression, the domains tend to align perpendicular to the stress axis.

Under this condition, any 90° domain wall motion, due to applied magnetic field, that increases the total magnetoelastic energy of the system will face a resistance. The presence of uniaxial compression, hence, tends to slow down the 90° domain wall motion. For the range of −50 MPa and −75 MPa, the combined effects of compressive stress-induced resistance of 90° domain wall motion and the momentary increase in the area of these walls seem to be the main cause of the spectral characteristics described above. With the magnitude of compressive stress beyond this range, less 90° domain walls are available and their motion becomes even slower to produce smaller peak amplitude of MAE burst. At the same time, the symmetry in the spectrum is restored.

Figure 10:
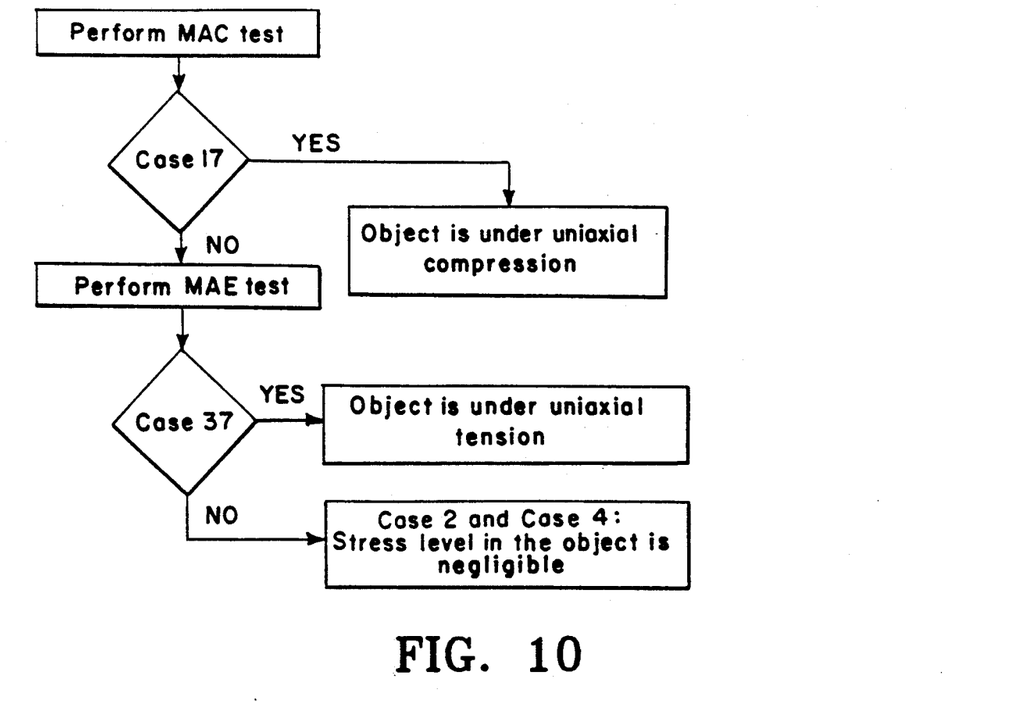
FIG. 10 is a block diagram illustrating the method of characterizing residual stress in a ferromagnetic test member (TM) in accordance with the invention.
Figure 11A:
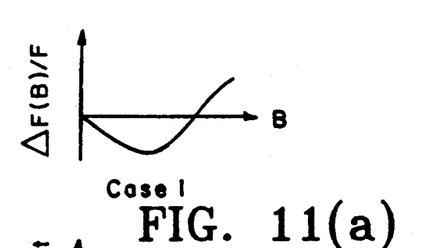
FIGS. 11(a)-(d) are diagrams illustrating the resulting waveforms used to both characterize the residual stress in a ferromagnetic test member (TM) and determine the uniaxial stress axis in the ferromagnetic test member (TM) on which applied.
Figure 11B:
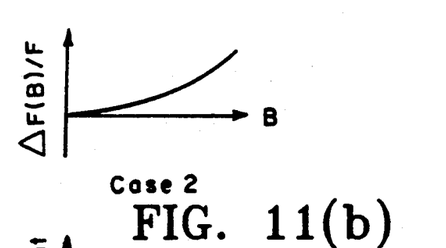

A preferred apparatus is shown in FIG. 9 for practicing the methods of this invention as previously described and as further illustrated in FIG. 10 and FIGS. 11a-b. The preferred circuit shown in FIG. 9 can be described by explaining the major differences in operation of the MAC and MAE measurement circuits which are activated by selector switch S when turned to position A or B respectively. All circuit components are known or commercially available and their operation need not be described in detail. The current path in the MAC and MAE circuits are identified by arrows A and B respectively. The MAC circuit uses a narrowband ultrasonic transducer 12, e.g., 5 MHz, 10 MHz, and so on, while the MAE circuit uses a broadband acoustic emission transducer 13 because acoustic noise contains many frequency components.

In the MAC circuit, ultrasonic pulses are generated and detected by transducer 12 but in the MAE circuit the acoustic emission transducer 13 passively detects the acoustic emission signals generated by magnetic domain wall motion.

In the MAC circuit, an external magnetic field is established by electromagnet EM when energized by a control voltage from signal generator 14 and PS/Amp PS. The control voltage is applied incrementally from zero to a maximum value in about a minute. An integrating fluxmeter FM measures the total magnetic flux in the test member TM while voltmeter VM measures the voltage, both results being sensed and stored in computer 23. In the MAC measurement circuit, the computer 23 is programmed to control the signal generator 14 and disconnect differential amplifier 8 by disconnecting switch S at position A. The computer also receives and stores the outputs from the fluxmeter FM and voltmeter VM. In the MAE measurement circuit, the computer 23 is programmed to connect differential amplifier 8 by connecting switch S at position B.

During this time, a pulsed-phase locked loop oscillator circuit (P2L2) 16 and frequency counter 17 measures the fractional changes in acoustic natural velocity (equivalent to the fractional changes in phase-locked ultrasonic waves) which changes are stored and displayed in computer 23.

In the MAE measurement circuit, an AC magnetic field is applied to test member TM when energized over many cycles of a sinewave control voltage generated by the signal generator 14. The frequency of the control voltage is regulated by computer 23.

The pickup coil PC is connected to the amplifier PS through differential amplifier 8 with switch S in position B to provide a feedback signal that assures the presence of the required magnetic field in the test member TM. The applied magnetic field follows the sinewave output voltage generated by the signal generator 14 the amplitude and frequency of which is controlled by computer 23.

As shown the MAC measurement technique measures the changes in acoustic natural velocity as a function of net magnetization induced in a ferromagnetic member. Since the acoustic waves create local stress, 90° domain walls respond to the acoustic waves by moving their positions and the process effectively reduces the elastic modulus of the material.

The application of an external magnetic field using the signal generator 14 changes magnetic domain structure, which in turn, modifies the availability of 90° domain walls that interact with the acoustic waves. This means that the elastic modulus varies continuously upon application of an external magnetic field. The domain structure before the application of the external field is predetermined uniquely based on the sign and magnitude of residual stress.

Depending on the residual stress states and the way the external magnetic field is applied, the availability of the 90° domain wall varies also uniquely. With simple model based on the above facts, it is shown that the elastic modulus decreases at the initial stage of magnetization process, when the magnetic field is applied parallel to the compressive uniaxial stress axis. In this particular condition, the elastic modulus reaches a minimum which corresponds to the maximum 90° domain wall area in the material, and with the field increases 90° walls begin to disappear as the sample approaches saturation.

For MAC measurements, the narrow band acoustic transducer 12 is used either in pitch-catch or pulse echo modes. The phase difference of the acoustic waves which are transmitted through the TM, reflected by the opposite wall, and travel back through the TM for reception, is proportional to the transit time of the waves in the sample which is directly related to the wave velocity, which, in turn is directly related to the elastic modulus. A known pulsed-phase-locked-loop (P2L2) oscillator circuit is used for the automated measurements of normalized acoustic velocity changes in the sample. As known, the actual parameters measured are the fractional frequency changes necessary to maintain the constant phase difference between the transmitted and received waves, while the wave speed changes. The frequency changes at an instant during the measurements are measured by the frequency counter 17 which interfaces to the desktop computer 23.

In accordance with the invention, and as shown in FIG. 10, the MAC circuit is first used to detect the presence (FIG. 11(a)) or absence (FIG. 11(b)) of uniaxial compressive stress without requiring a calibration standard. As previously described, this is because of the discovery of a negative initial slope of frequency change as a function of applied field to net magnetic induction as shown in FIG. 11(a). This unique effect of uniaxial compressive stress for MAC measurements has been proven to be universal, i.e., for any kind of steel sample regardless of its treatment history or impurity concentration. The MAC measurement circuit, however, as demonstrated is not effective in detecting or distinguishing the presence of uniaxial tensile stress as shown in FIGS. 7 and 8 and as possibly illustrated in FIG. 11(b).

In accordance with the invention, the MAE measurement technique uses a broad band acoustic transducer 13 for passive detection of acoustic noise generated by the motion of magnetic domain walls induced by an AC external magnetic field. This acoustic noise is detected by transducer 13, the output of which is amplified in a pre-amp 19 and processed in a digitizer 21 and a multi-channel analyzer 22 for storage and display in a desktop computer 23. The digitizer 21 is provided as a redundant check of the output of the multi-channel analyzer 22.

As is known, the MAE spectral characteristics of the resulting acoustic noise pattern largely depends upon the structure of magnetic domains. Any stress, other than hydrostatic pressure, affects the domain structure of a ferromagnetic test member TM in a certain way to minimize the total system interaction energy. There exists two types of magnetic domain walls in iron base ferromagnetic materials, which include nearly any type of steel; 90° and 180° domain walls. The motion of 90° domain walls cause change in local strain field which releases elastic energy that can be detected as acoustic noise signals by a transducer.

Only 90° domain walls respond to stress by moving their positions such that the interaction energy between the magnetic and lattice system can be minimized. Tensile stress applied to a steel sample removes most of the 90° domain walls and the domain structure is dominated by the 180° walls. With an application of AC magnetic field under this condition, the motion of 180° walls is the major magnetization mechanism which does not create any substantial acoustic noise. The experimental results have shown that this effect is sensitive to the tensile stress magnitude.

The magnetoacoustic emission MAE signals detected by the acoustic emission transducer 13 are displayed as shown in FIGS. 1, 2, 3 and 5 on an oscilloscope 20 for a first step visual check before being fed into the multi-channel analyzer 22, a Series Plus multi-channel analyzer made by Canberra Industrious, Inc., Meriden, Conn. A pulse height distribution analysis is performed in accordance with a known technique to produce a histogram waveform of the MAE spectra.

Figure 11C:
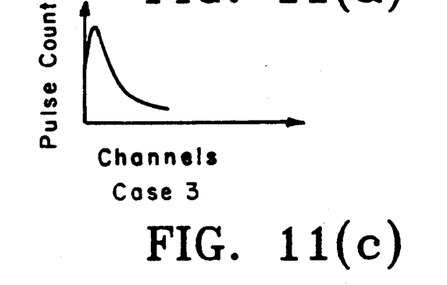

The histogram, which is stored and displayed as a waveform in computer 23, is fitted to a governing theoretical equation as explained to yield certain parameter values that determine the shape of the pulse height distribution curve as illustrated in the waveforms in FIGS. 4 and 11(c) and (b).

As discovered, and as explained, the pulse height or amplitude distribution becomes narrower with an increased amplitude of tensile stress as shown in FIG. 11(c). The presence of an initial narrow and high peak in the pulse height distribution waveform signifies the presence of an undesirably high tensile residual stress.

This is because the effect of compressive stress, as has been discovered, is to be very small in the generation of MAE signals.

It is thus shown that MAE measurements are insensitive to uniaxial compression. However, there exists a possibility that a highly compressed state can be mistaken as a stress state with a low magnitude tension. To avoid such a conclusion, it is important to first know whether the test member TM is under residual compression, which is determined by using the MAC measurement technique as shown in the first step of FIG. 10.

Figure 11D:
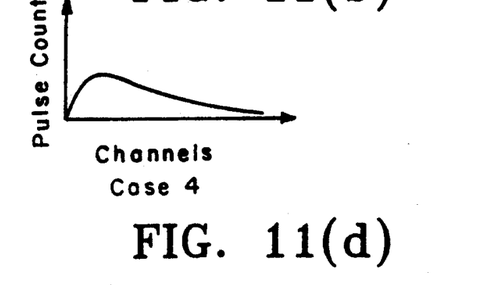

Assuming an absence of compressive residual stress in the test member TM, switch S is selectively turned from position A to position B to conduct an MAE measurement as described. As shown in FIGS. 4 and 11(c) the MAE measurement clearly shows the difference between the unstressed state and that under tension. If the resulting MAE spectrum results in a histogram waveform as shown in FIG. 11(d) then the residual stress in the test member TM is negligible or zero. Thus the invention includes two novel features: (1) a unique application of an MAE measurement technique for the detection of residual tensile stress; and (2) the combined use of the unique MAE measurement technique and the MAC technique to provide method and apparatus for characterizing residual uniaxial stress in structural ferromagnetic members, mainly steel.

The many features and advantages of the present invention are apparent from the detailed specification, and thus, it is intended by the appended claims to cover all such features and advantages of the method an apparatus which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. A method of characterizing residual stress in a ferromagnetic test member comprising the steps of:
   applying a DC magnetic field that varies in strength from zero to a maximum value over a determined interval of time to said test member;
   simultaneously applying a beam of acoustical energy to said test member to produce an acoustical energy propagation through said test member;
   sensing as a waveform the changes of velocity in the acoustical energy propagation at selected times during said determined time interval;
   relating said resulting changes in the velocity of the acoustical energy propagation to the forces producing residual stress in said test member, the initial slope of said waveform from zero to a small value of applied DC magnetic field characterizing the residual stress in said test member, wherein a negative initial slope in the waveform indicates significant compressive residual stress in said test member, and wherein a positive initial slope in the waveform indicates either the presence of significant tensile residual stress in said test member or a negligible stress condition in said test member;
   applying an AC magnetic field to said test member over a subsequent, determined time interval;
   simultaneously sensing as a pulse histogram acoustical emission signals generated in said test member resulting from the applied AC magnetic field; and relating the resulting pulse histogram to residual stress in said test member to distinguish between tensile residual stress and either compressive residual stress or a negligible residual stress condition, wherein a relatively high and narrow initial peak in the histogram indicates a significant tensile residual stress in said test member.

2. The method of claim 1 wherein an initial lower and wider crown in the pulse histogram indicates a negligible residual stress condition in said test member.

3. The method of claim 1, wherein the DC magnetic field is applied parallel to a uniaxial stress axis in said test member.

4. The method of claim 1 wherein the DC magnetic field is applied perpendicular to a uniaxial stress axis in said test member.

5. The method of claim 1 wherein the AC magnetic field is applied parallel to a uniaxial stress axis in said test member.

6. The method of claim 1 wherein the AC magnetic field is applied perpendicular to a uniaxial stress axis in said test member.

7. The method according to claim 1, wherein said step of applying the magnetic field to said test member comprises applying the magnetic field such that it increases incrementally from zero to the maximum value.

8. A method for characterizing residual stress in a ferromagnetic test member comprising the steps of:
applying an AC magnetic field to said test member over a determined time interval;
simultaneously sensing as a pulse histogram acoustical emission signals generated in said test member resulting from the applied AC magnetic field; and
relating the resulting pulse histogram to the residual stress in said test member to distinguish between tensile residual stress and either compressive residual stress or a negligible residual stress condition, a relatively high and narrow initial peak in the pulse histogram indicating a significant tensile residual stress in said test member.

9. The method according to claim 8, wherein an initial lower and wider crown in the pulse histogram signifies a negligible residual stress condition in said test member.

10. The method of claim 8 wherein the AC magnetic field is applied parallel to a uniaxial stress axis in said test member.

11. The method of claim 8 wherein the AC magnetic field is applied perpendicular to a uniaxial stress axis in said test member.

* * * * *